US011944765B2

(12) United States Patent
Rizik et al.

(10) Patent No.: US 11,944,765 B2
(45) Date of Patent: Apr. 2, 2024

(54) TRANSSEPTAL PUNCTURE DEVICE AND METHOD OF USE

(71) Applicant: Bedrosian Global, LLC, Malibu, CA (US)

(72) Inventors: David Rizik, Scottsdale, AZ (US); Bert Bedrosian, Malibu, CA (US); Erik Sorensen, Chaska, MN (US); Andrew Senn, Chaska, MN (US)

(73) Assignee: BEDROSIAN GLOBAL, LLC, Malibu, CA (US)

( * ) Notice: Subject to any disclaimer, the term of this patent is extended or adjusted under 35 U.S.C. 154(b) by 114 days.

(21) Appl. No.: 17/101,559

(22) Filed: Nov. 23, 2020

(65) Prior Publication Data
US 2021/0154435 A1 May 27, 2021

Related U.S. Application Data

(60) Provisional application No. 62/938,833, filed on Nov. 21, 2019.

(51) Int. Cl.
A61M 25/06 (2006.01)
A61M 25/00 (2006.01)

(52) U.S. Cl.
CPC ...... *A61M 25/065* (2013.01); *A61M 25/0026* (2013.01); *A61M 25/0662* (2013.01);
(Continued)

(58) Field of Classification Search
CPC . A61B 17/34; A61B 17/3415; A61B 17/3478; A61B 5/150396;
(Continued)

(56) References Cited

U.S. PATENT DOCUMENTS 3,064,651 A * 11/1962 Henderson .......... A61M 5/3286
604/274
4,808,170 A * 2/1989 Thornton .............. A61M 5/158
604/274
(Continued)

FOREIGN PATENT DOCUMENTS

CN 206576930 U 10/2017
WO 2013101632 A1 7/2013
WO 2018175743 A1 9/2018

OTHER PUBLICATIONS

Int'l Search Report and Written Option in Int'l. Appl. No. PCT/US20/61786 dated Feb. 12, 2021.
(Continued)

*Primary Examiner* — Kami A Bosworth
(74) *Attorney, Agent, or Firm* — Jeffer Mangels; Butler & Mitchell LLP; Brennan C. Swain, Esq.

(57) ABSTRACT

A transseptal puncture system that includes a needle member that includes a distal end, a proximal end and defines a first lumen therethrough, a dilator that includes a distal end, a proximal end and defines a second lumen therethrough, a sheath that includes a distal end, a proximal end and defines a third lumen therethrough, a needle control device that is configured to move the needle member a predetermined distance from a stowed position to a deployed position and a guidewire that includes a distal end and a proximal end and is movable within the first lumen. The needle member is movable within the second lumen and the distal end of the needle member is configured to puncture the septum. The dilator is movable within the third lumen.

8 Claims, 19 Drawing Sheets

(52) U.S. Cl.
CPC ............... *A61M 2025/0681* (2013.01); *A61M 2025/0687* (2013.01); *A61M 2210/125* (2013.01)

(58) Field of Classification Search
CPC ... A61B 2017/3454; A61B 2017/3456; A61M 5/3286; A61M 25/0169; A61M 25/0172; A61M 25/06; A61M 25/0606; A61M 25/065; A61M 25/0662; A61M 2025/0004; A61M 2025/0062; A61M 2025/0681; A61M 29/00; A61M 2210/125; A61M 2205/195
See application file for complete search history.

(56) References Cited

U.S. PATENT DOCUMENTS

| | | | |
|---|---|---|---|
| 6,277,100 | B1 | 8/2001 | Rauelson |
| 6,702,791 | B1* | 3/2004 | Hilgers ............. A61B 10/0045 604/274 |
| 7,666,203 | B2 | 2/2010 | Chanduszko |
| 7,678,081 | B2 | 3/2010 | Whiting |
| 8,337,518 | B2 | 12/2012 | Nance |
| 8,961,550 | B2 | 2/2015 | Lenker |
| 9,440,054 | B2 | 9/2016 | Bishop |
| 9,463,268 | B2 | 10/2016 | Spence |
| 9,861,802 | B2 | 1/2018 | Mickelsen |
| 9,980,812 | B2 | 5/2018 | Wilson |
| 10,058,312 | B2 | 8/2018 | Lalonde |
| 2006/0064062 | A1 | 3/2006 | Gurusamy et al. |
| 2006/0135962 | A1 | 6/2006 | Kick et al. |
| 2007/0270741 | A1 | 11/2007 | Hassett |
| 2008/0154217 | A1* | 6/2008 | Carrez ................... A61L 27/50 604/272 |
| 2010/0036409 | A1 | 2/2010 | Scheib |
| 2011/0054487 | A1 | 3/2011 | Farnan |
| 2012/0239069 | A1 | 9/2012 | Benscoter |
| 2014/0188108 | A1 | 7/2014 | Goodine |
| 2017/0014159 | A1 | 1/2017 | Stokes |
| 2018/0085142 | A1 | 3/2018 | Leeflang et al. |
| 2018/0250477 | A1* | 9/2018 | Mueller ............. A61M 5/3286 |
| 2019/0167305 | A1 | 6/2019 | Pedersen |

OTHER PUBLICATIONS

European Search Report, 20891109.9 / 4061258 PCT/US2020061786, dated Oct. 18, 2023.

* cited by examiner

TRANSSEPTAL PUNCTURE DEVICE AND METHOD OF USE

CROSS REFERENCE TO RELATED APPLICATIONS

This application claims the benefit of U.S. Provisional Application No. 62/938,833, filed Nov. 21, 2019, the entirety of which is incorporated herein by reference.

FIELD OF THE INVENTION

The present invention relates generally to a device for creating a transseptal puncture.

BACKGROUND OF THE INVENTION

Certain catheter based procedures (e.g., valve and left atrial procedures) require a transseptal puncture so that a catheter can be advanced from the right atrium of the heart to the left atrium. The typical transseptal technique requires that a catheter (e.g., an SL-1 or similar 8 French catheter) is passed from a vein in the leg to the right atrium. At the level of the right atrium a hole is created or a puncture is made (known as septostomy) between the right atrium and the left atrium (in the atrial wall or septum) in order to gain access the left atrium. This technique is called transseptal puncture.

Conventionally, the 8 French SL-1 catheter has one of several types of "needles" or radiofrequency ablation (RFA) catheters manually placed in it for the purpose of creating the hole in the septum. That hole is generally made with either a needle, as in the case of the Brockenbrough technique, or a radiofrequency puncture of the septum, as in the Baylis technique. Once the hole in the atrial septum is created, the needle (Brockenbrough versus Baylis) is advanced across the septum from the right atrium to the left atrium. Due to the fact that the needle has a sharp leading edge, advancing the needle into the left atrium includes the risk of puncturing the wall of the left atrium, which can cause bleeding complications.

Generally, once the hole is created in the septum or transseptal puncture is made, and after the needle has been passed into the left atrium, the SL-1 catheter is also advanced over the needle into the left atrium. The needle is then retracted and, a 0.032 inch (blunt) J-tipped guidewire is then advanced through the SL-1 catheter and is placed in the left atrium and/or the left upper pulmonary vein which communicates with the left atrium. It will be appreciated that all these devices (SL-1 catheter, needle and guidewire) are separate devices and are inserted separately during the procedure, as described above. PCT Publication No. WO 2013/101632A1 (PCT App No. PCT/US2012/70813) is incorporated by reference herein in its entirety.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a transseptal puncture system that includes a needle member that includes a distal end, a proximal end and defines a first lumen therethrough, a dilator that includes a distal end, a proximal end and defines a second lumen therethrough, a sheath that includes a distal end, a proximal end and defines a third lumen therethrough, a needle control device that is configured to move the needle member a predetermined distance from a stowed position to a deployed position and a guidewire that includes a distal end and a proximal end and is movable within the first lumen. The needle member is movable within the second lumen and the distal end of the needle member is configured to puncture the septum. The dilator is movable within the third lumen.

In a preferred embodiment, the needle member includes a needle wall having inner and outer surfaces and a distal end. The first lumen is defined by the inner surface of the needle wall. The distal end includes an inner edge surface, an outer edge surface and a transverse leading edge surface. The inner edge surface is non-parallel with the outer edge surface, and the transverse leading edge surface has a transverse dimension that is equal to or less than half a thickness of the needle wall. In a preferred embodiment, the inner and outer edge surfaces are flat. In another preferred embodiment, the inner and outer edge surfaces are curved. In an embodiment with curved inner and outer edge surfaces, the inner edge surface defines a radius that is between 0.05 and 0.5 times the thickness of the needle wall, and the outer edge surface defines a radius that is between 0.05 and 0.5 times the thickness of the needle wall. In another embodiment, only one of the inner and outer edge surfaces may define these curved dimensions. The curved dimensions of the inner and outer edge surfaces can be different or one or the other can be flat.

In a preferred embodiment, the needle control device includes a deployment member. Preferably, the deployment member is movable between a first position and a second position (an electrical switch or the like meets this definition). Movement of the deployment member from the first position to the second position moves the distal end of the needle member from the stowed position to the deployed position. In a preferred embodiment, the deployment member is movable within a slot that includes a first position stop member and a second position stop member. Preferably, the distance of travel of the deployment member between the first and second stop members defines the predetermined distance of travel of the distal end of the needle member from the stowed position to the deployed position. It will be appreciated that there may be some "play" or slight difference (within 1-2 millimeters) between the movement of the deployment member between the first and second positions and the movement of the distal end of the needle member between the stowed and deployed positions.

In accordance with another aspect of the present invention there is provided a method performed in a heart that (a) obtaining a transseptal puncture device that includes a sheath, a dilator, a needle member, a guidewire and a needle control device. The guidewire is positioned in a first lumen defined in the needle member, the needle member is positioned in a second lumen defined in the dilator, and the dilator is positioned in a third lumen defined in the sheath. The needle control device is configured to move the needle member between a stowed position and a deployed position. The method includes (b) moving a distal end of the dilator into the right atrium, (c) moving the needle member from the stowed position to the deployed position using the needle control device, such that the needle member is advanced out of a distal opening in the distal end of the dilator, (d) puncturing the septum with a distal end of the needle member to create a septum opening, and (e) advancing the guidewire out of an opening in the distal end of the needle member and into the left atrium.

In a preferred embodiment, the method may also include moving the distal end of the dilator through the septum opening and into the left atrium, moving the needle member from the deployed position to the stowed position using the needle control device, such that the distal end of the needle member is retracted into the second lumen, removing the dilator and needle member, and loading a component (for performing a procedure in the heart) onto the guidewire and advancing the component over the guidewire and through the third lumen.

The present invention is a transseptal puncture device and system that includes a catheter, a needle member and a guidewire. Generally, the transseptal needle member, which is housed in the lumen of the dilator or catheter (e.g., SL-1 catheter) includes a guidewire (e.g., 0.025" guidewire) disposed therein. During use, the guidewire is used to cross the atrial septum, thus alleviating the need for the prior art sharp tipped transseptal needle to be advanced into the left atrium. In other words, when the needle or RFA catheter penetrates the septum, immediately the preloaded (or pre-contained) guidewire is passed into the left atrium and/or left upper pulmonary vein as it is already preloaded in the lumen of the needle or RFA catheter.

Accordingly, the present invention includes a transseptal penetration system by which a preloaded J-tipped guidewire-in-needle system (i.e., needle lumen accommodating the preloaded 0.025" guidewire) is utilized for the purposes of performing a septostomy and ameliorating the need for a sharp transseptal needle to be advanced into the left atrium as is currently performed. The transseptal needle member comes with (and houses within its lumen) a preloaded J-tipped guidewire for transsepetal crossing. It will be appreciated that the invention described herein includes both the transseptal puncture device and the method or procedure for using the device.

The present invention provides deflectable tip technology, minimal left atrial protrusion is required during use, rapid, and safe guidewire deployment. In a preferred embodiment, the transseptal needle system components include a pre-curved, hollow-lumen, RF puncture needle, and a transseptal guidewire. In a preferred embodiment, the device limits the distal needle throw, minimizing the risk of free wall perforation and pericardial effusion. In other words, the distal end of the needle has a pre-set or predetermined travel limit.

In a preferred embodiment, the circumferential hollow-lumen needle tip provides or facilitates smooth advancement through the inner dilator surface and prevents adverse engagement with the mating guidewire. The circumferential hollow-lumen needle tip preferably includes inner and outer edge radii or surfaces that allow the needle to move smoothly into and out of the dilator (the outer edge radii or surface) and allows the guidewire to enter and exit the needle lumen smoothly (the inner edge radii or surface). For example, in a preferred embodiment, the circumferential outer edge radius of the distal surface or end of the needle has a dimension between 0.05 and 0.5 times the wall thickness of the hollow-lumen needle and the circumferential inner edge radius of the distal surface or end of the needle has a dimension between 0.05 and 0.5 times the wall thickness of the hollow-lumen needle. In a preferred embodiment, the transverse leading edge dimension of the hollow-lumen needle does not exceed 0.5 times the wall thickness of the needle.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
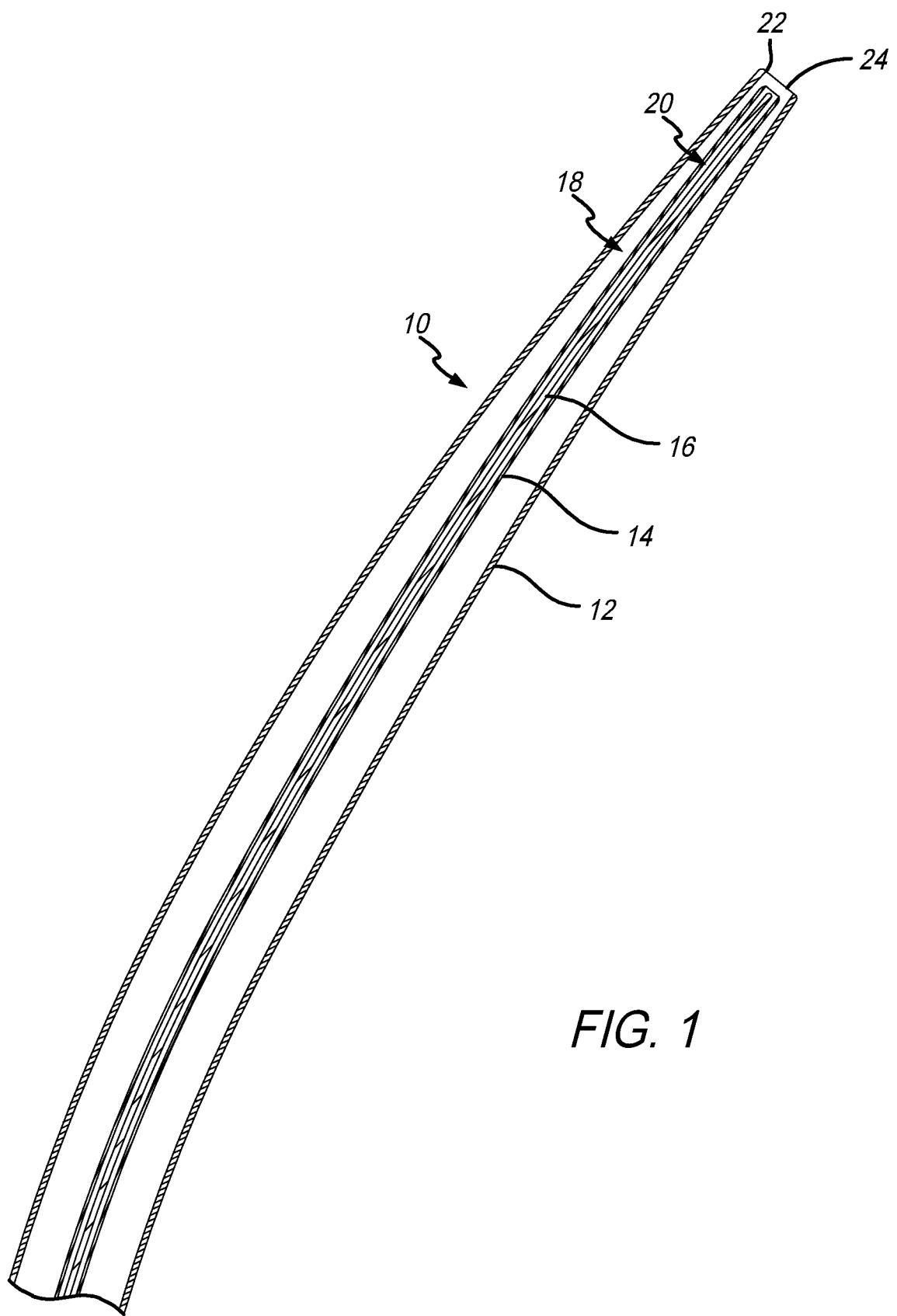
FIG. 1 is a cross sectional view of a transseptal puncture device in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the-disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

With reference to the attached drawings, FIGS. 1-9 show a transseptal puncture system or device 10 in accordance with a preferred embodiment of the present invention. The invention also includes a method and procedure for using the transseptal puncture system, as shown in FIGS. 4-9, in a human heart 100 that includes a right atrium 102, left atrium 104 and a septum 106.

As shown in FIG. 1, in a preferred embodiment, the transseptal puncture system 10 includes a catheter or dilator 12, a needle member 14 and a guidewire 16. The needle member 14 defines a central or first lumen 20 with the guidewire 16 positioned therein. The dilator 12 defines a central or second lumen 18 that houses the needle member 14

Figure 2:
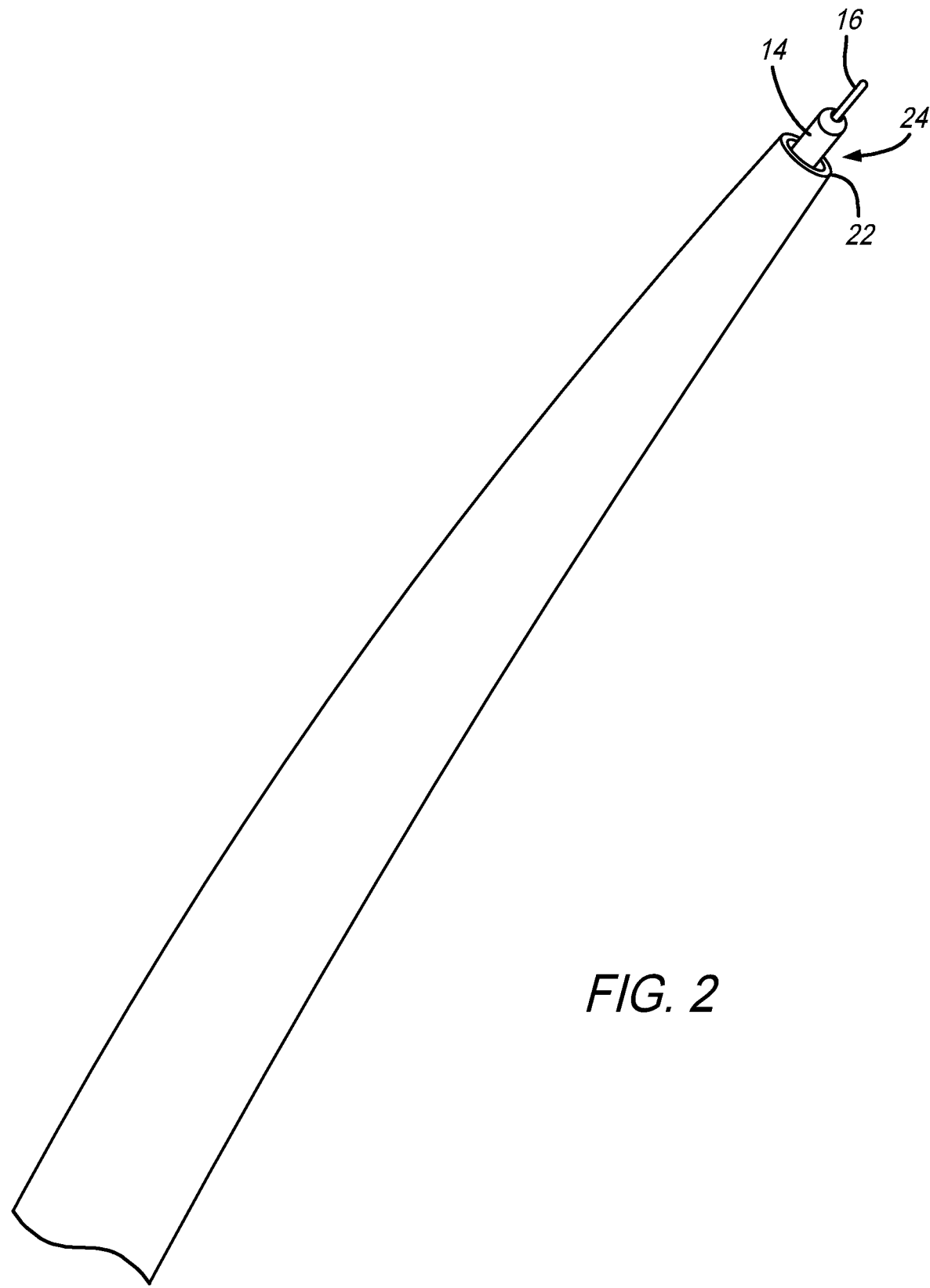
FIG. 2 is a perspective view of the transseptal puncture device with the needle member extending outside of the dilator or catheter and the guidewire extending outside of the needle member.

As shown in FIG. 2, in a preferred embodiment, the dilator 12 includes distal end 22 that includes a distal opening 24 in the end thereof that allows the needle member 14 and guidewire 16 to exit the dilator 12 during use. Preferably, the distal end portion of the dilator tapers. The dilator 12 includes a main body portion that has an outer diameter and the distal end 22 has a smaller outer diameter. The outer diameter of the dilator tapers from the main body portion (constant diameter portion) to the distal end 22.

Figure 3:
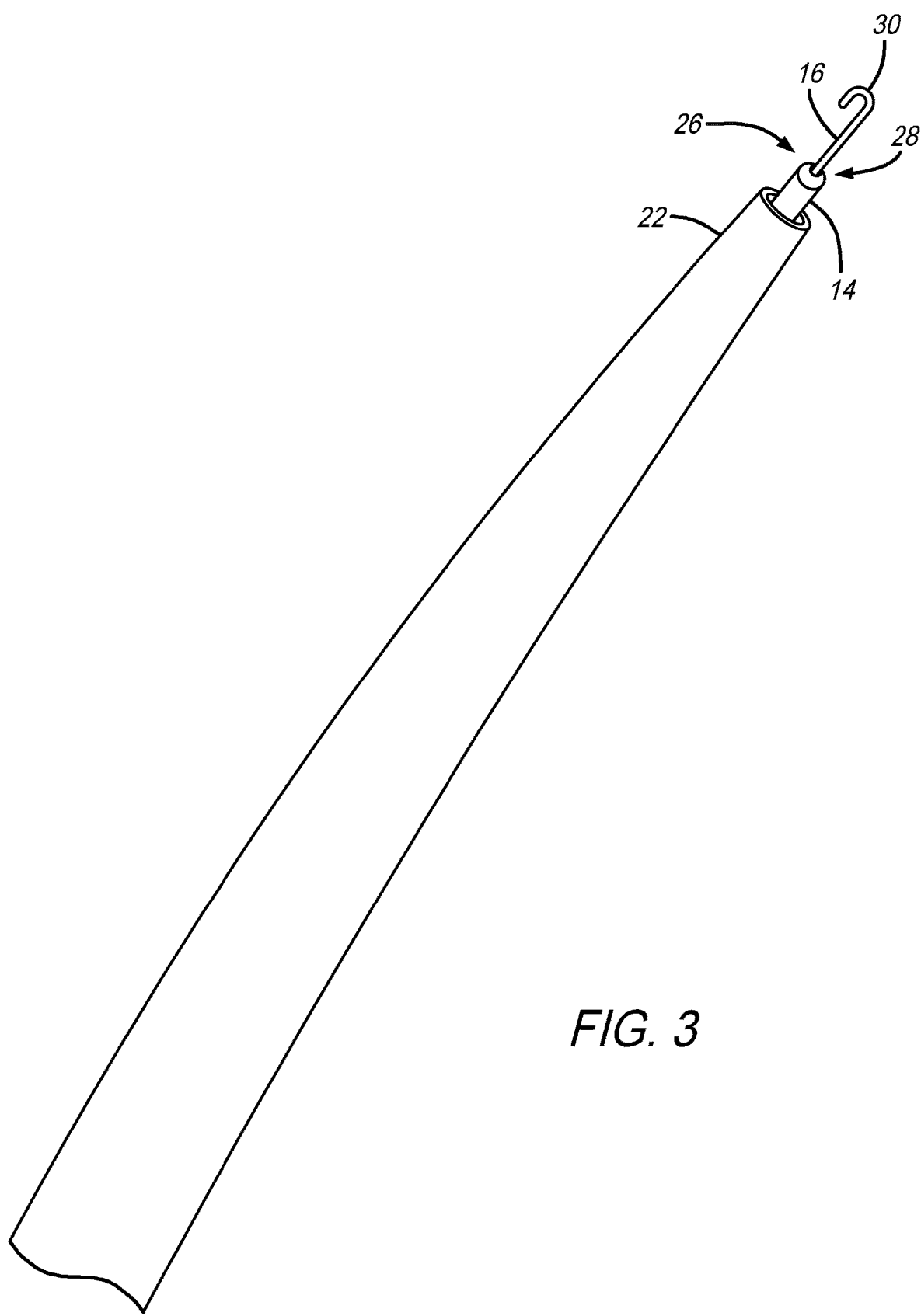
FIG. 3 is a perspective view of the transseptal puncture device with the guidewire having a J-shaped tip.

As shown in FIG. 3, in a preferred embodiment the needle member 14 includes a tapered distal end 26 and a distal opening 28 therein that allows the guidewire 16 to exit the needle member during use. In a preferred embodiment, the distal end 26 of the needle member 14 is sharp enough to puncture the septum and create a septum opening. In another preferred embodiment, the distal end 26 of the needle member 14 can be configured to burn through the septum using RFA to create the puncture and septum opening. In this embodiment, the distal end 26 of the needle member 14 is not sharp. In a preferred embodiment, the guidewire 16 includes a J-shaped, curved or spiraled tip 30 that takes its shape after it has exited the needle member 14. This protects from the guidewire puncturing any of the walls of the heart.

Figure 4:
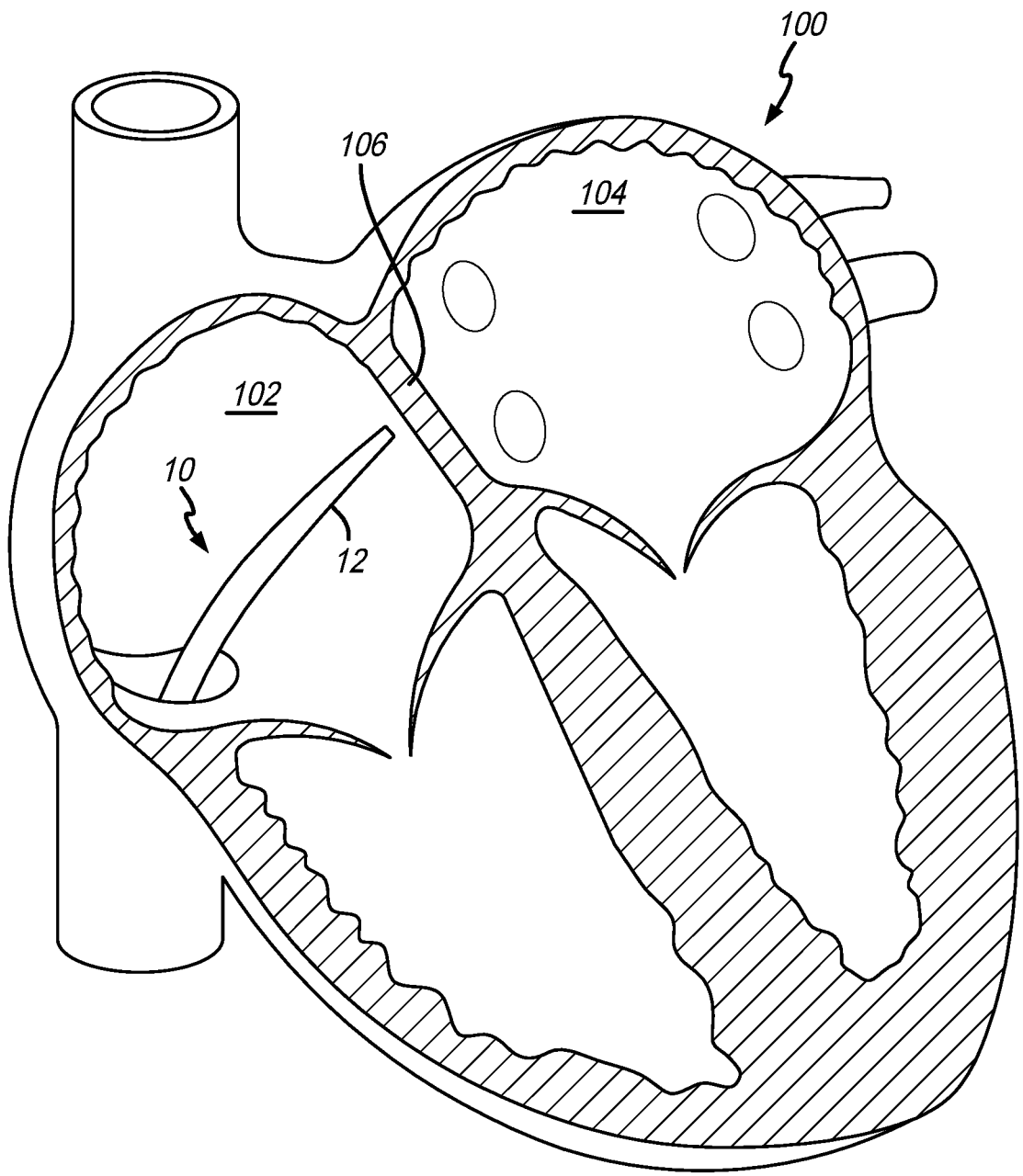
FIG. 4 shows the transseptal puncture device positioned in the right atrium of a heart.
Figure 5:
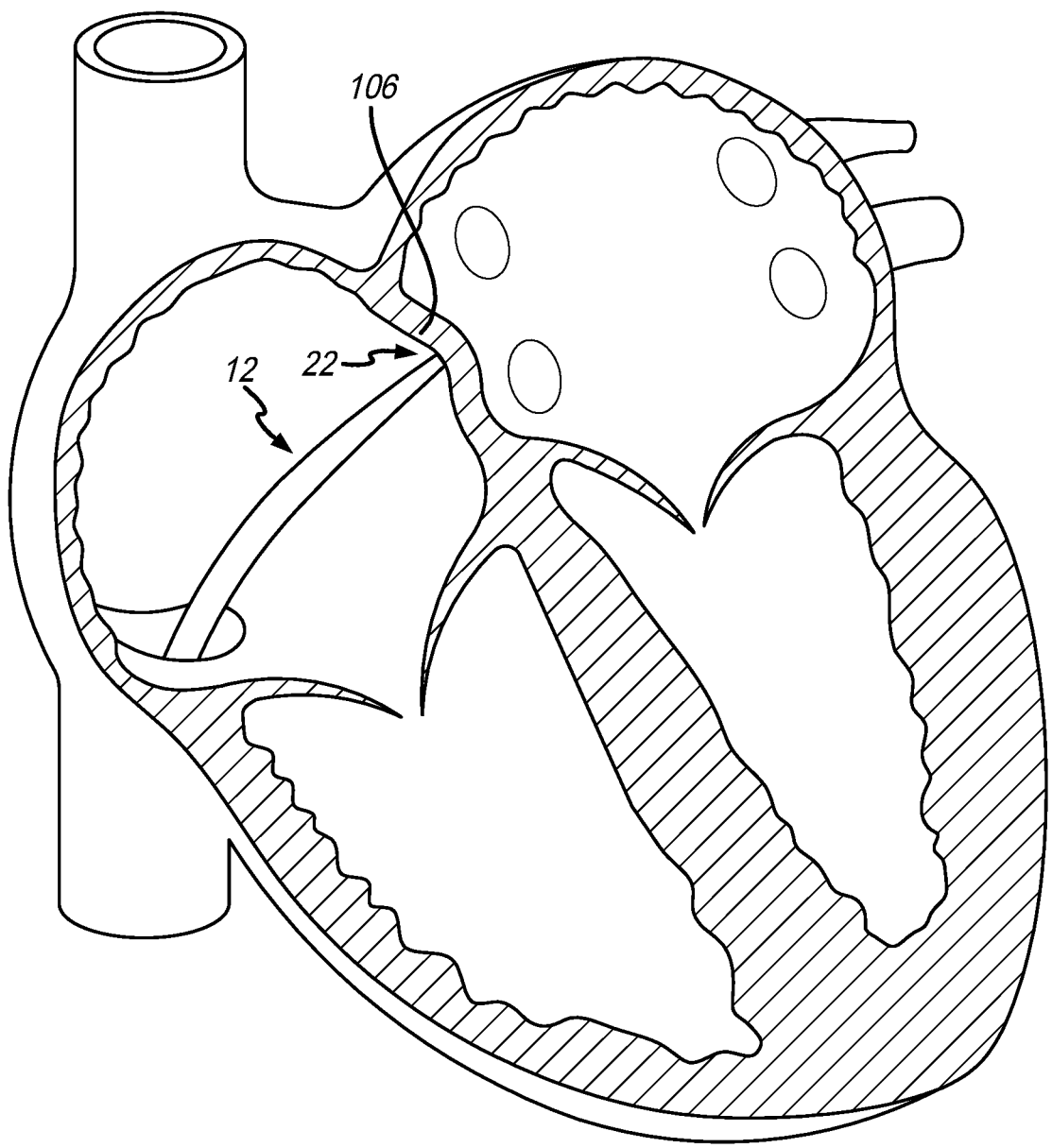
FIG. 5 shows the transseptal puncture device positioned against the septum.
Figure 6:
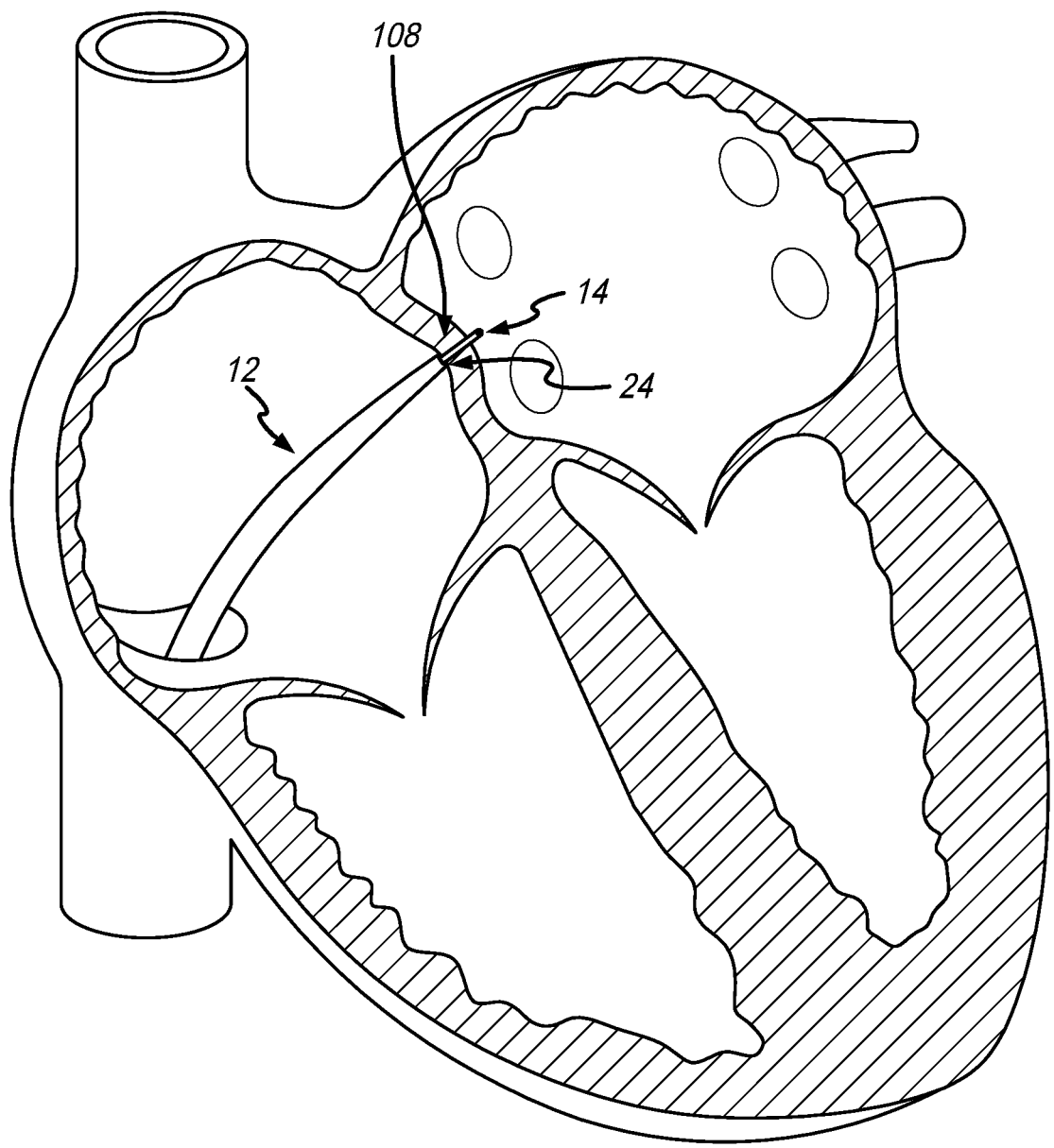
FIG. 6 shows the needle member advanced out of the opening in the end of the dilator and puncturing the septum.

FIGS. 4-9 show a series of steps for using the transseptal puncture system 10 to puncture the septum and advance the guidewire 16 into the left atrium. As shown in FIG. 4, the transseptal puncture system 10 is first advanced by a user into and positioned in the right atrium 102. It will be appreciated by those of ordinary skill in the art that the dilator 12 (together with the needle member 14 and guidewire 16) enters the body through the femoral artery. However, this is not a limitation on the invention, and the catheter can be inserted through other entry points. As shown in FIG. 5, next, the distal end 22 of the dilator 12 is pressed against the septum 106 (a process known as tenting). As shown in FIG. 6, the needle member 14 is then moved within the second lumen 18 and advanced out of the distal opening 24 in the end of the dilator 12 and is used to puncture the septum 106 to create the septum opening 108.

Figure 7:
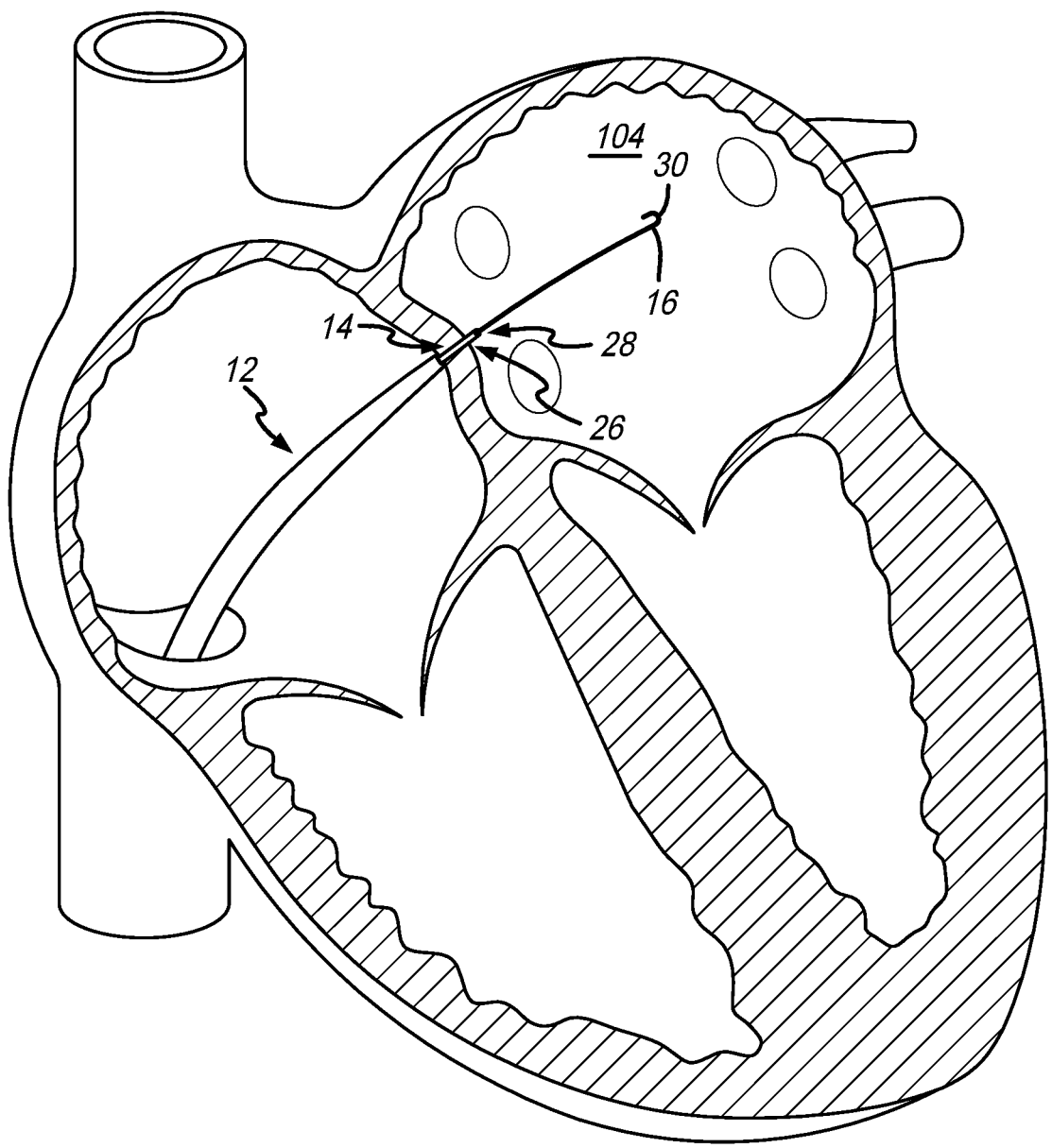
FIG. 7 shows the guidewire advanced through the opening in the distal end of the needle member and into the left atrium.

After the septum has been punctured, as shown in FIG. 7, the guidewire 16 is then moved within the first lumen 20 and advanced through the distal opening 28 in the distal end 26 of the needle member 14 and into the left atrium 104. As the guidewire 16 exits the needle member, the distal end of the guidewire 16 forms a J-shape 30 to prevent it from puncturing the wall of the heart. In a preferred embodiment, once the needle member 14 punctures the septum it is not advanced any further into the left atrium. As is described above, in the prior art, the needle is often advanced relatively far into the left atrium (at least as far as the J-tip 30 of the guidewire shown in FIG. 7). This risks puncturing the far wall. In a preferred embodiment, the distal end of the needle member 14 is never advanced past a plane bifurcating the left atrium.

Figure 8:
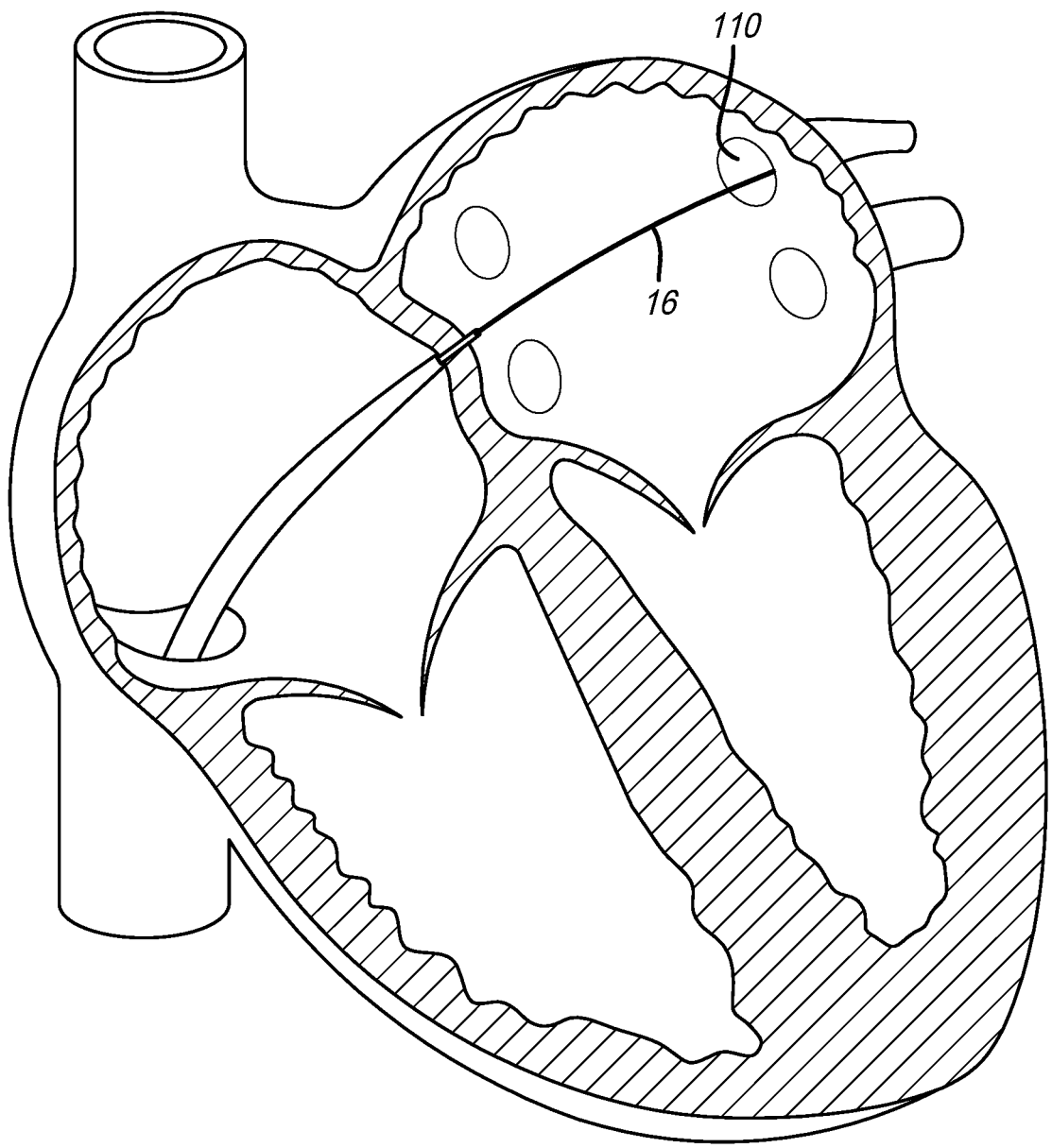
FIG. 8 shows the guidewire advanced into the left upper pulmonary vein.
Figure 9:
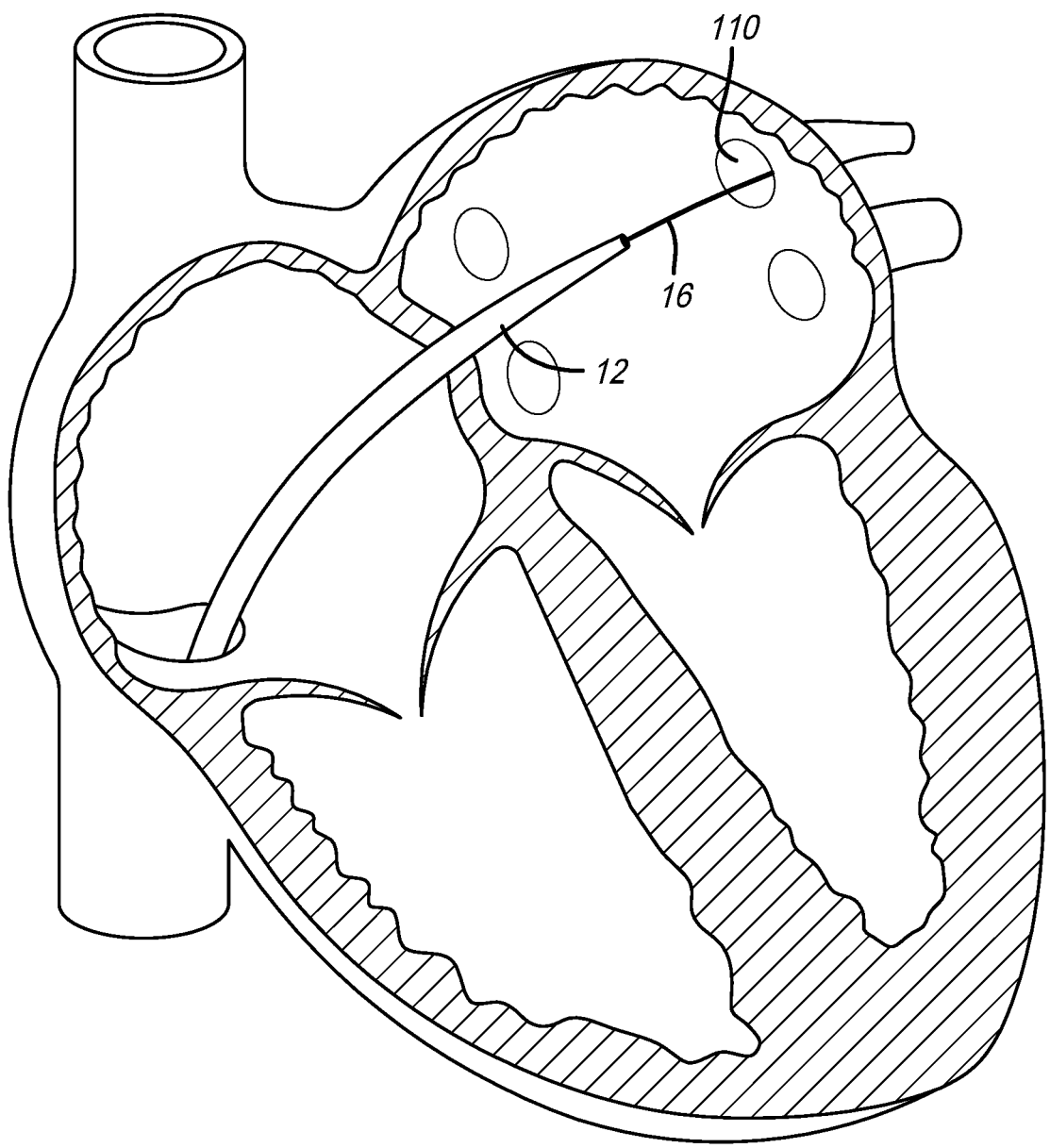
FIG. 9 shows the dilator advanced further into the left atrium so that the desired component or device can be delivered to the left atrium.

FIG. 8 shows an optional step in the procedure where the guidewire 16 is advanced into the left upper pulmonary vein 110. This allows the guidewire 16 to take a position that allows other components to be advanced over the guidewire after the needle member has been retracted, as described below. Once the guidewire 16 has been advanced to the desired location the needle member 14 can be retracted. FIG. 9 shows the dilator 12 being advanced further into the left atrium so that the desired component or device can be delivered to the left atrium. It will be appreciated that other components can be advanced over the guidewire and through the dilator 12 or both the dilator 12 and needle member 14 can be retracted over the guidewire and another catheter can be advanced over the guidewire for insertion of another component.

Figure 10:
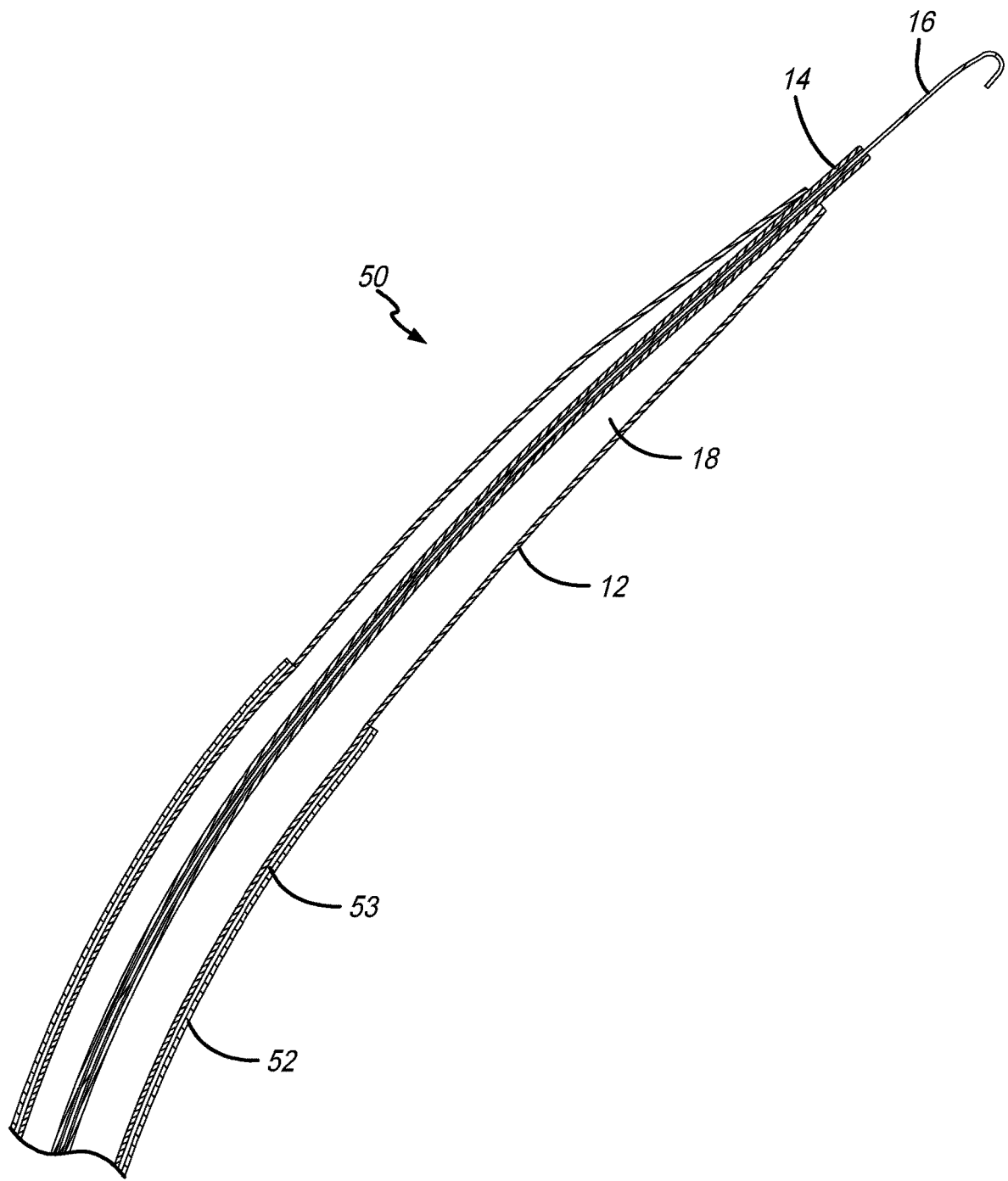
FIG. 10 is a perspective view of a second embodiment of the transseptal puncture device with the needle member extending outside of the dilator, the dilator extending outside of the sheath and the guidewire extending outside of the needle member.
Figure 11:
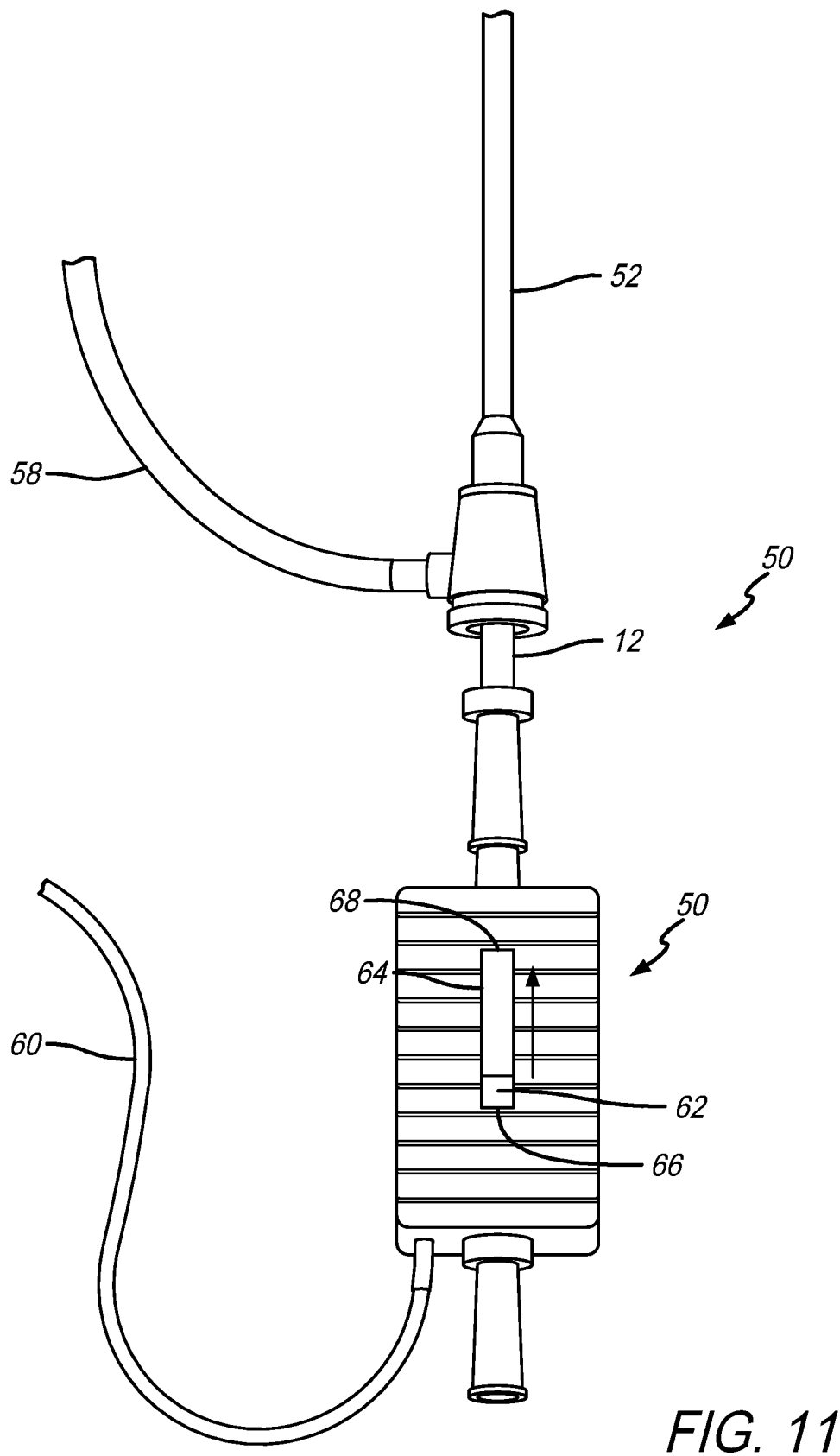
FIG. 11 is a perspective view of a portion of the transseptal puncture device shown in FIG. 10, showing the needle control device.

FIGS. 10-11 show another embodiment of a transseptal puncture system or device 50 in accordance with a preferred embodiment of the present invention. As shown in FIGS. 10-11, in a preferred embodiment, the transseptal puncture system 50 includes a sheath 52, a catheter or dilator 12, a needle member 14, a guidewire 16 and a needle control device 56. The sheath 52 defines a third lumen 53. The transseptal puncture system 50 is similar to the embodiment described above, but includes the needle control device 56 that controls movement of the needle member 14 between a stowed position where the needle member 14 is completely inside the lumen of the dilator (e.g., see FIG. 1), and a stowed position, as shown in FIG. 10, where the distal end of the needle member 14 is outside the dilator 12.

It will be appreciated that the needle control device 56 allows controlled movement of the needle member 14. The deployed position allows the needle member to advance far enough out of the dilator 12 that it punctures the septum, but not far enough that it can cause damage to the walls of the heart. In a preferred embodiment, the distal end of the needle member cannot move past the deployed position (in a distal direction).

The needle control device 56 can be any device or mechanism that allows movement of the needle member in and out of the lumen of the dilator. FIG. 11 shows a linear switch or deployment member 62 that moves forwardly and backwardly to move the needle member 14 between the deployed and stowed positions. Movement of the needle control device or deployment member 62 from the first position to the second position moves the needle member 14 from the stowed position to the deployed position. The proximal end of the needle member 14 is operatively connected to the needle control device or linear switch. For example, a cable can extend between the needle control device or linear switch and the needle member. In a preferred embodiment, the deployment member 62 is movable within a slot 64 that includes a first position stop member 66 and a second position stop member 68. When the deployment member 62 is moved distally (see the arrow in FIG. 11), the second position stop member 68 stops the deployment member 62, thus preventing the needle member 14 from moving beyond the deployed position. The distance of the movement of the deployment member 62 is less than the width of the left atrium of the heart of the patient. Moreover, the distance of the movement of the deployment member 62 is less than the width of the left atrium of the heart of any potential patient.

The needle control device can also be an electrical switch, lever, button or other mechanism. The system 50 can also include a tube 58 for providing blood pressure measurements, and a cord 60 if the needle member is configured for radio frequency ablation. In use, the dilator and needle member (together with the needle control device) can be disconnected from the sheath as a unit so that other components can be delivered through the sheath and/or over the guidewire.

Figure 12A:
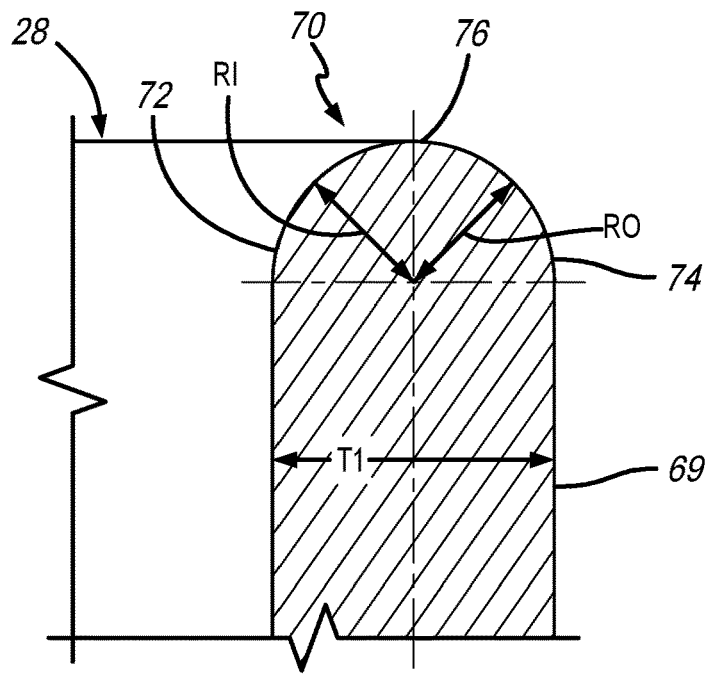
FIG. 12A is a cross-section of a portion of the distal end of the needle member in accordance with a preferred embodiment of the present invention.
Figure 12B:
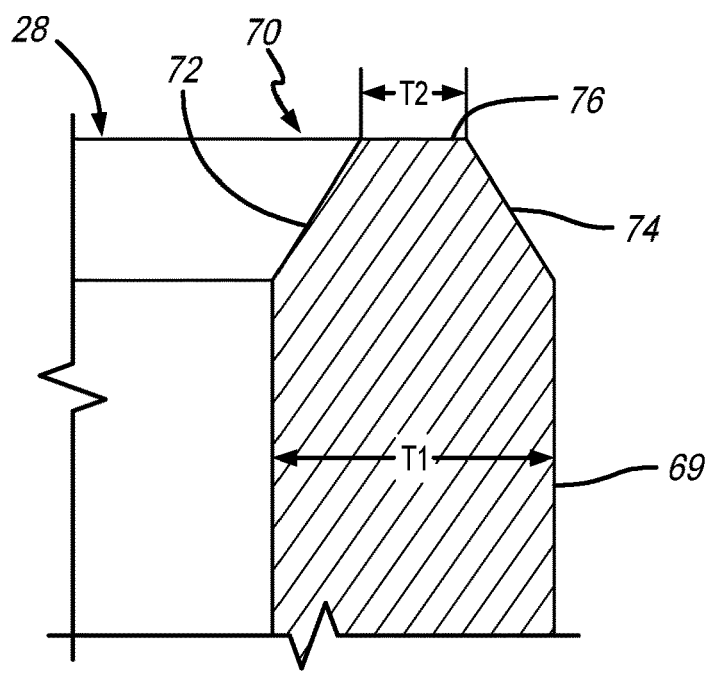
FIG. 12B is a cross-section of a portion of the distal end of the needle member in accordance with a preferred embodiment of the present invention.

With reference to FIGS. 12A and 12B, in a preferred embodiment, the distal end of the needle member is configured or designed so that it facilitates smooth advancement through the inner dilator surface 54a and prevents adverse engagement with the mating guidewire 16. As shown in FIGS. 12A and 12B, the distal tip or end 70 of the needle member wall 69 includes inner and outer edge surfaces 72 and 74 that are curved and include radii (FIG. 12A), are flat (FIG. 12B) or a combination thereof. The inner edge surface 72 at least partially defines the distal opening 28 of the needle member 14. In an embodiment with curved inner and outer edge surfaces 72 and 74, the inner edge surface radius RI of the distal end of the needle member 14 has a dimension between 0.05 and 0.5 times the wall thickness T1 of the needle member 14 and the outer edge surface radius RO of the distal end of the needle member 14 has a dimension between 0.05 and 0.5 times the wall thickness T1 of the needle member 14. As shown in FIG. 12B, in a preferred embodiment, the dimension of the transverse leading edge surface 76 of the needle member 14 has a transverse dimension T2 that does not exceed 0.5 times the wall thickness of the needle. In the embodiment of FIG. 12A, T2 is essentially the very tip or distal end of the needle wall where the inner and outer edge surface radii meet.

Figure 13:
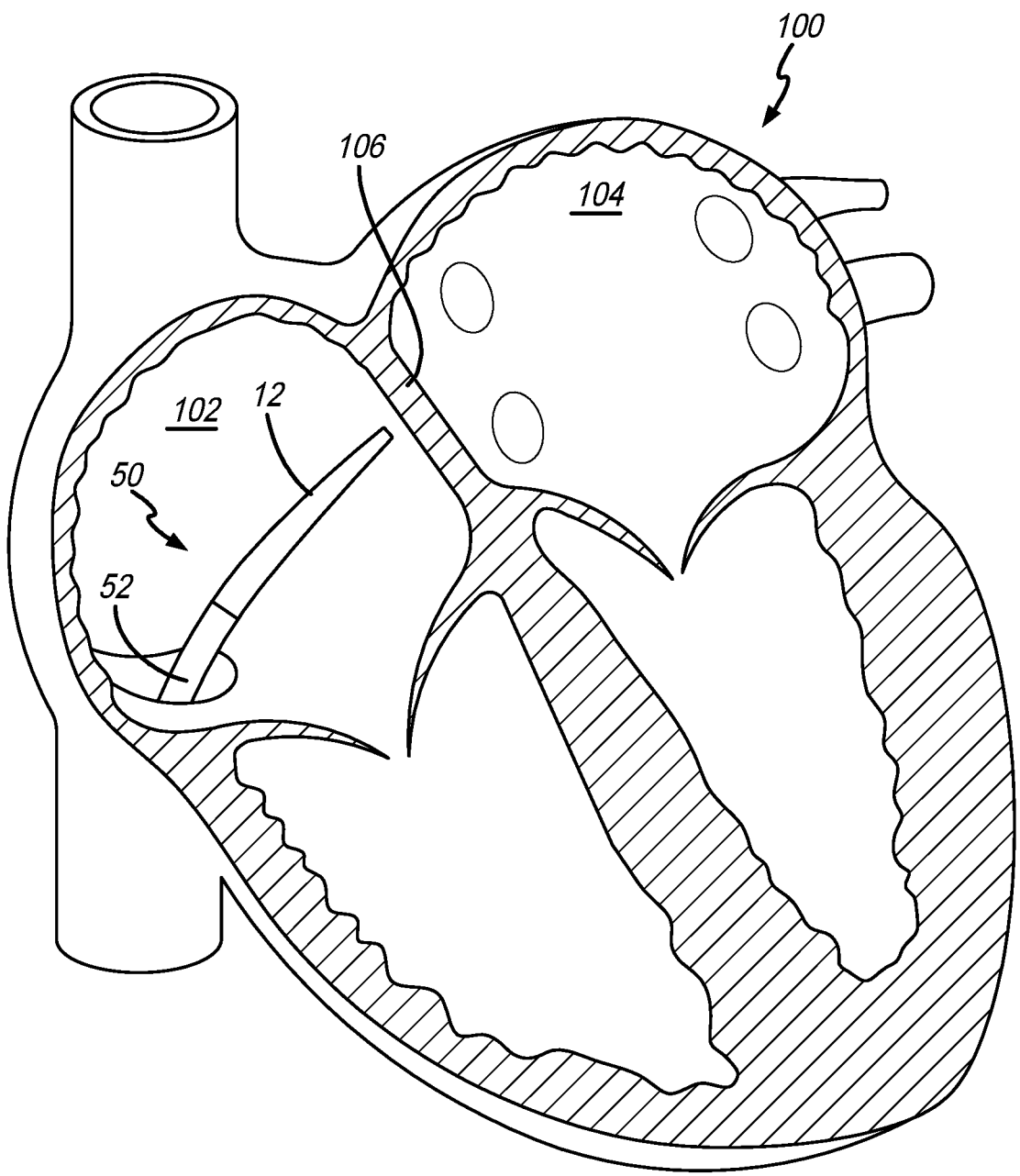
FIG. 13 shows the transseptal puncture device of the second embodiment positioned in the right atrium of a heart.
Figure 14:
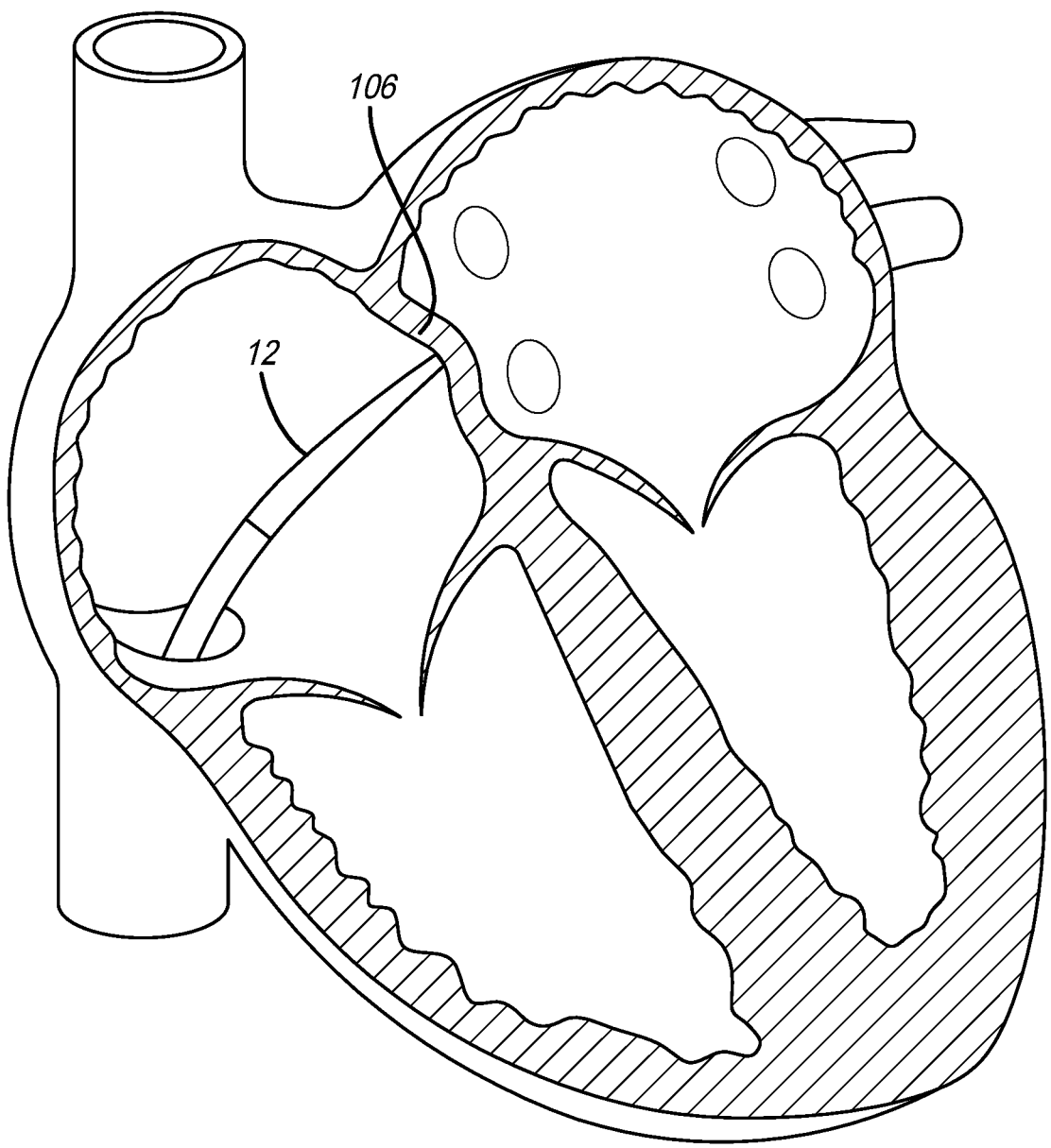
FIG. 14 shows the transseptal puncture device positioned against the septum.
Figure 15:
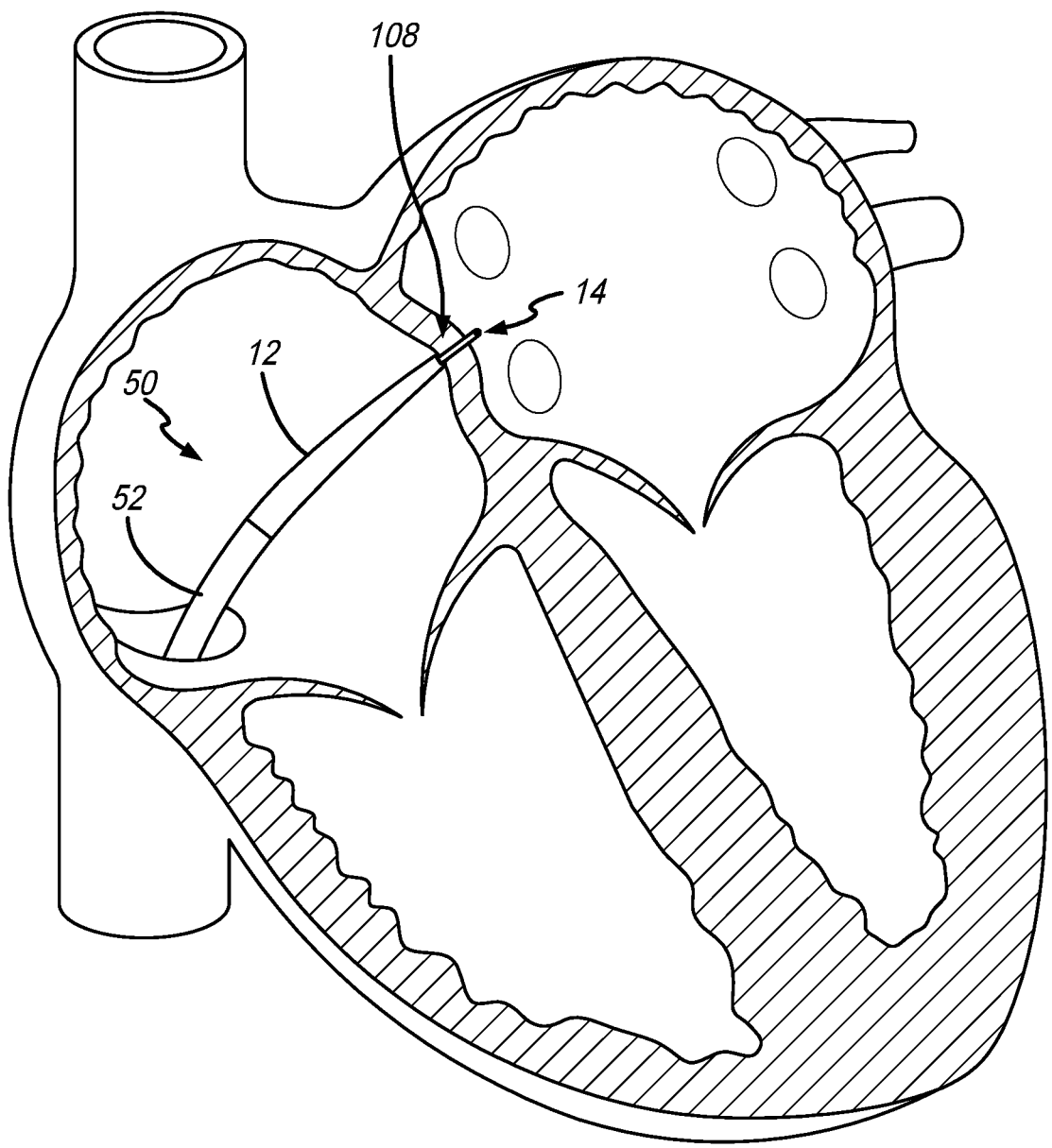
FIG. 15 shows the needle member advanced out of the opening in the end of the dilator and puncturing the septum.

FIGS. 13-19 show a series of steps for using the transseptal puncture system 50 to puncture the septum and advance the guidewire 16 into the left atrium. As shown in FIG. 13, the transseptal puncture system 50 is first advanced by a user into and positioned in the right atrium 102. It will be appreciated by those of ordinary skill in the art that the sheath 52 (together with the dilator 12 needle member 14 and guidewire 16) enters the body through the femoral artery. However, this is not a limitation on the invention, and the catheter can be inserted through other entry points. As shown in FIG. 14, next, the distal end of the dilator 12 is pressed against the septum 106 (a process known as tenting). As shown in FIG. 15, the needle member 14 is then moved from the stowed position to the deployed position by the needle control device 56 and advanced out of the distal opening in the end of the dilator 12 and is used to puncture the septum 106 to create the septum opening 108.

Figure 16:
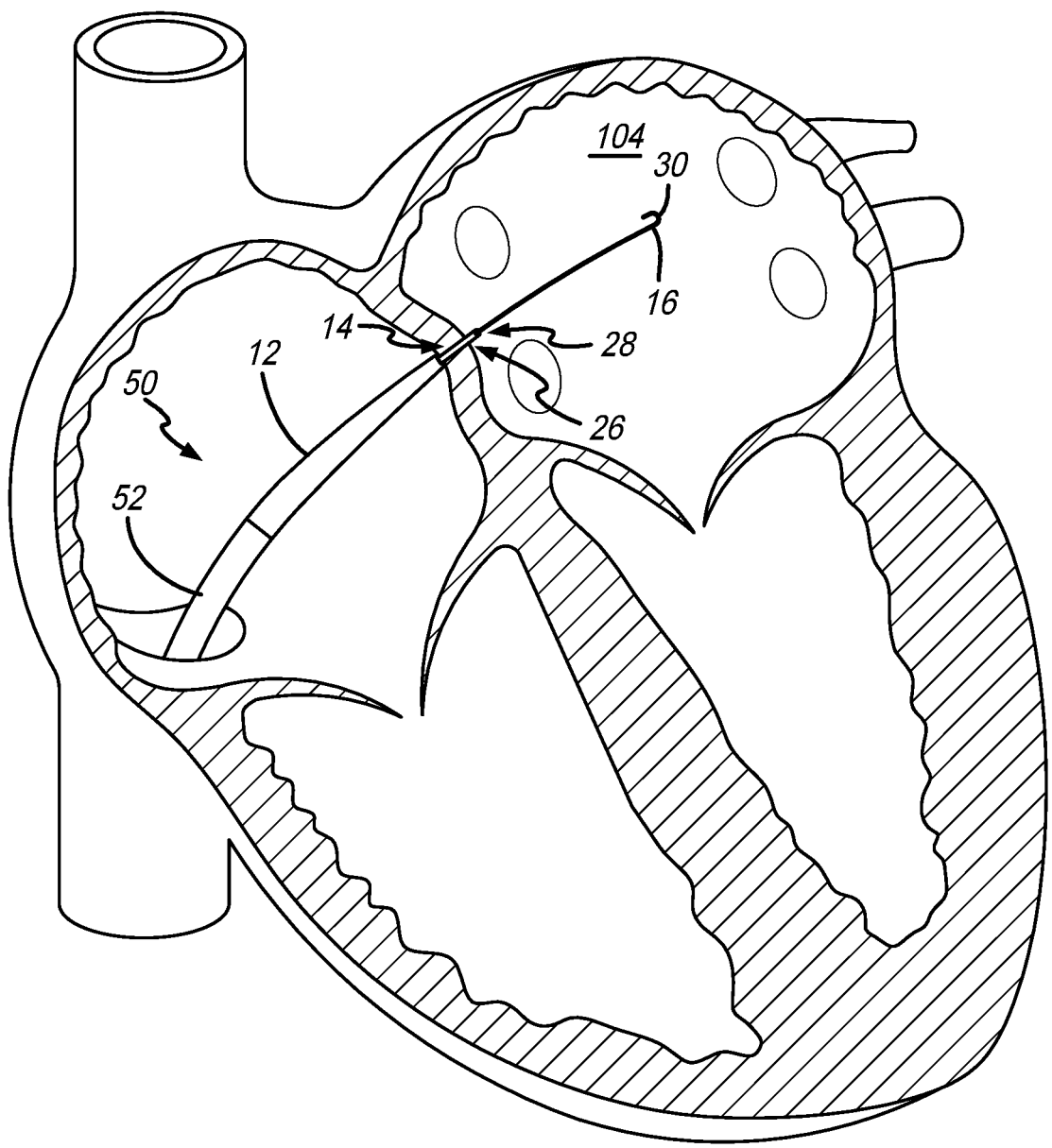
FIG. 16 shows the guidewire advanced through the opening in the distal end of the needle member and into the left atrium.

After the septum has been punctured, as shown in FIG. 16, the guidewire 16 is then moved within the first lumen 20 and advanced through the distal opening in the distal end of the needle member 14 and into the left atrium 104. As the guidewire 16 exits the needle member, the distal end of the guidewire 16 forms a J-shape 30 to prevent it from puncturing the wall of the heart. Due to the control or stroke of the needle control device 56, once the needle member 14 punctures the septum it is not advanced any further into the left atrium. As is described above, in the prior art, the needle is often advanced relatively far into the left atrium (at least as far as the J-tip 30 of the guidewire shown in FIG. 16). This risks puncturing the far wall. In a preferred embodiment, the distal end of the needle member 14 is never advanced past a plane bifurcating the left atrium.

Figure 17:
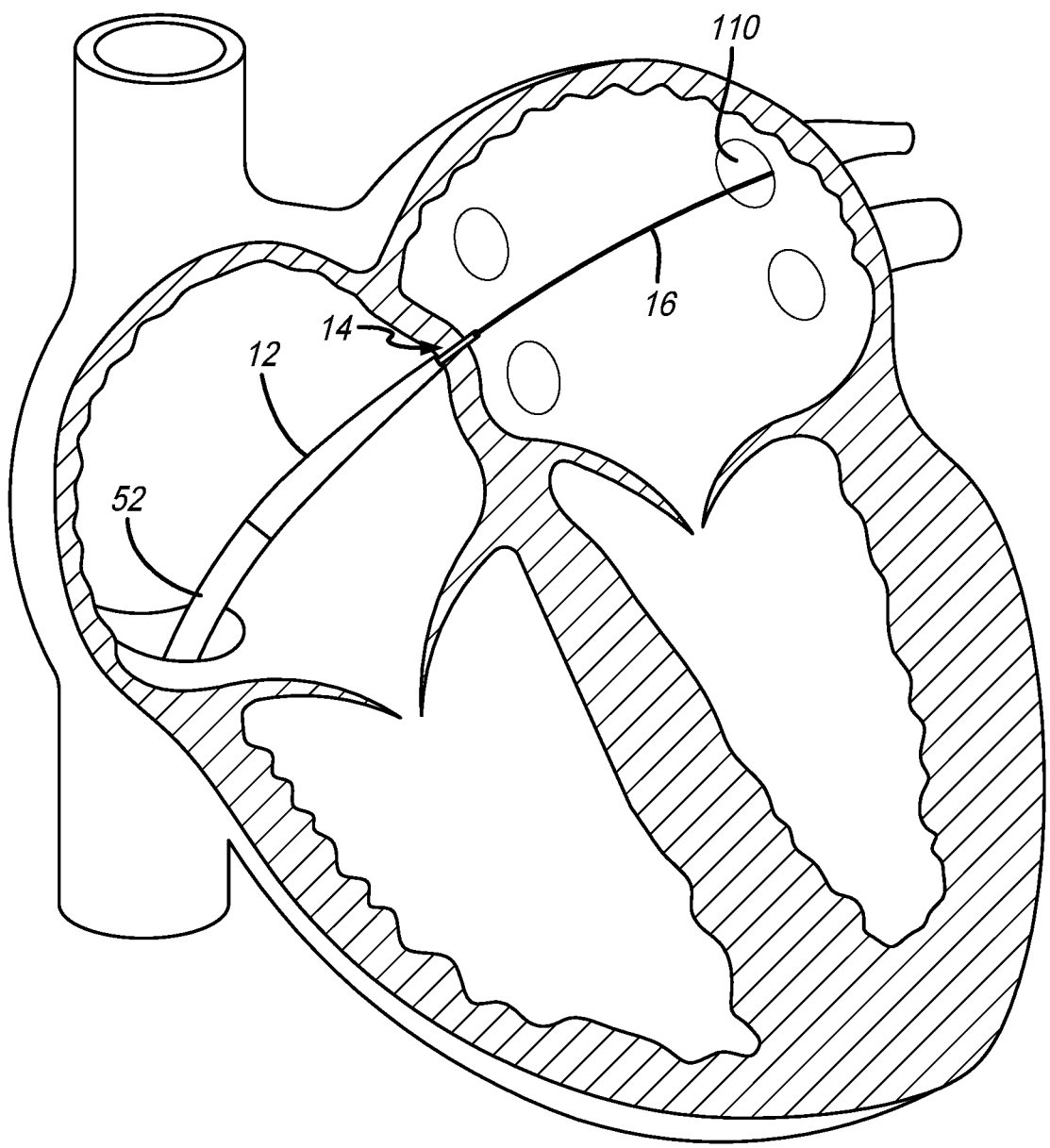
FIG. 17 shows the guidewire advanced into the left upper pulmonary vein.
Figure 18:
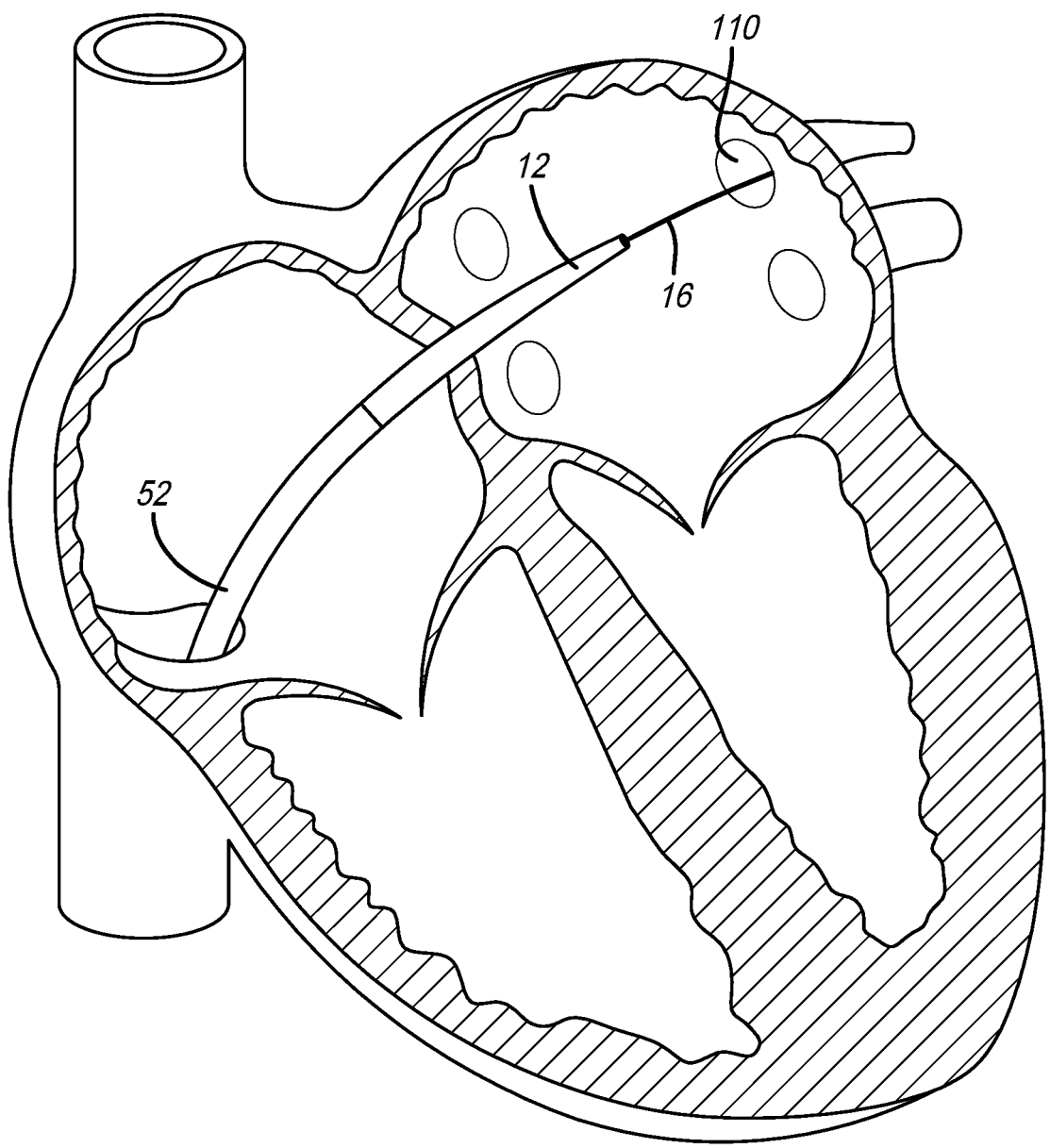
FIG. 18 shows the dilator advanced further into the left atrium to dilate the septal puncture.

FIG. 17 shows an optional step in the procedure where the guidewire 16 is advanced into the left upper pulmonary vein 110. This allows the guidewire 16 to take a position that allows other components to be advanced over the guidewire after the needle member has been retracted, as described below. Once the guidewire 16 has been advanced to the desired location the needle member 14 can be retracted to the stowed position using the needle control device 56. FIG. 18 shows the dilator 12 being advanced further into the left atrium to dilate the septal puncture and so that the desired component or device can be delivered to the left atrium. It will be appreciated that other components can be advanced over the guidewire and through the sheath 52 after retraction of the dilator 12 and needle member 14.

Figure 19:
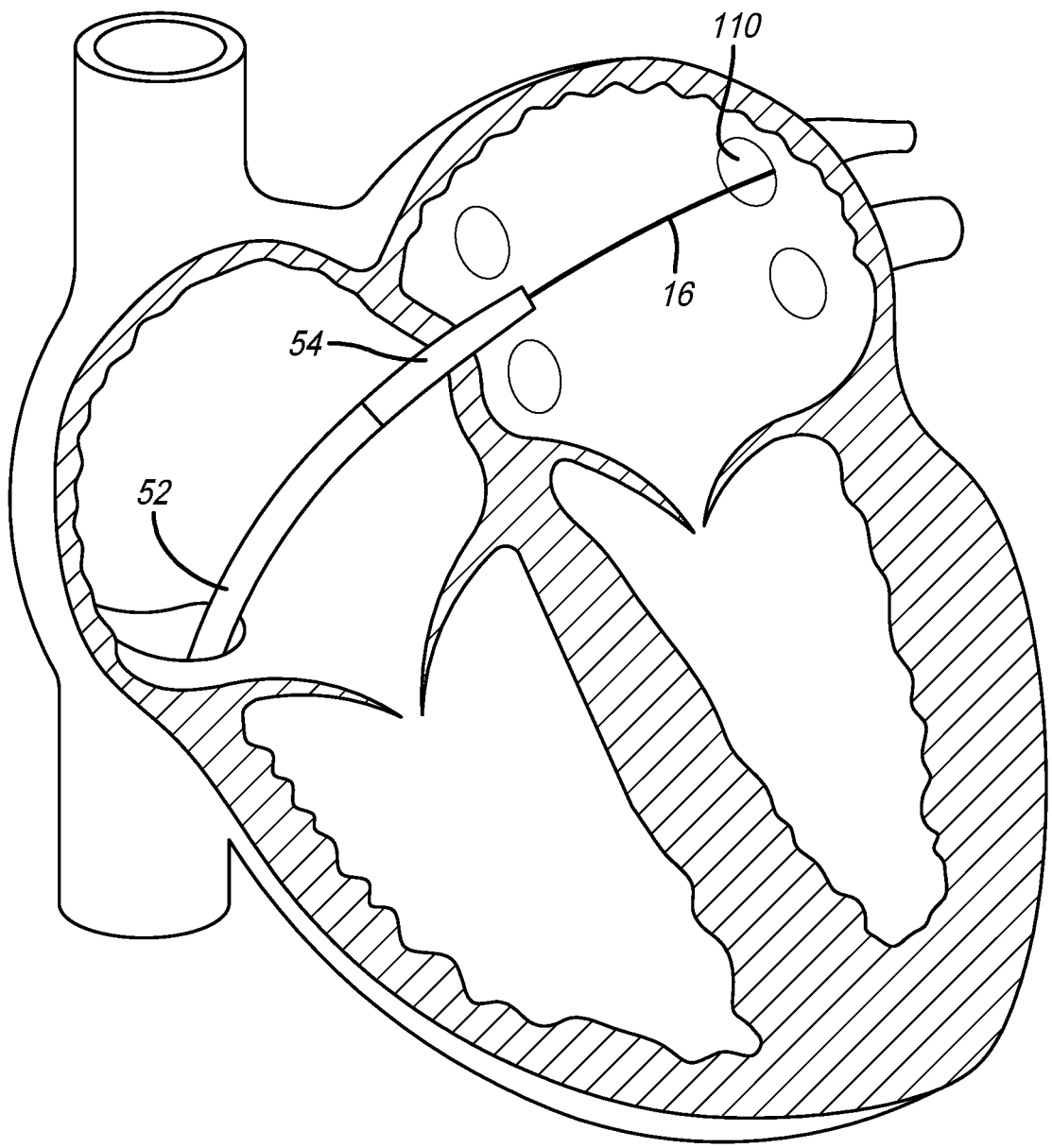
FIG. 19 shows a heart procedure component being advanced into the left atrium after removal of the dilator and needle member.

After the step shown in FIG. 18, the dilator 12 and needle member 14 are retracted or removed from and through the sheath 52 and a component 54 for use in a heart procedure is loaded onto the guidewire 16 and into the sheath and advanced over the guidewire, through the third lumen and into the left atrium, as shown in FIG. 19.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A transseptal puncture system for use in a heart having a septum, the transseptal puncture system comprising:
a needle member that includes a distal end and a proximal end, wherein the needle member defines a first lumen therethrough and defines a needle axis, wherein the needle member includes a cylindrical needle wall that includes inner and outer surfaces and a distal end, wherein the first lumen is defined by the inner surface of the needle wall, wherein the distal end of the needle wall includes an inner edge surface, an outer edge surface and a circular shaped transverse leading edge surface, wherein the inner edge surface is non-parallel with the outer edge surface, wherein the inner edge surface is curved and extends between the circular shaped transverse leading edge surface and the inner surface, wherein the outer edge surface is curved and extends between the circular shaped transverse leading edge surface and the outer surface, wherein a leading edge plane is defined by the circular shaped transverse leading edge surface, and wherein the leading edge plane extends perpendicular to the needle axis, a dilator that includes a distal end and a proximal end, wherein the dilator defines a second lumen therethrough, wherein the needle member is movable within the second lumen, and wherein the distal end of the needle member is configured to puncture the septum, a sheath that includes a distal end and a proximal end, wherein the sheath defines a third lumen therethrough, wherein the dilator is movable within the third lumen, a needle control device that is configured to move the needle member a predetermined distance from a stowed position to a deployed position, and a guidewire that includes a distal end and a proximal end and is movable within the first lumen.

2. The transseptal puncture system of claim 1 wherein the transverse leading edge surface has a transverse dimension that is equal to or less than half a thickness of the needle wall.

3. The transseptal puncture system of claim 2 wherein the inner edge surface defines a radius that is between 0.05 and 0.5 times the thickness of the needle wall, and wherein the outer edge surface defines a radius that is between 0.05 and 0.5 times the thickness of the needle wall.

4. The transseptal puncture system of claim 1 wherein the needle control device includes a deployment member.

5. The transseptal puncture system of claim 4 wherein the deployment member is operatively connected to the needle member and is movable between a first position and a second position, wherein movement of the deployment member from the first position to the second position moves the distal end of the needle member with respect to the dilator from the stowed position to the deployed position.

6. The transseptal puncture system of claim 5 wherein the deployment member is movable within a slot, wherein the slot includes opposite first and second ends, wherein the first end of the slot defines a first position stop member and the second end of the slot defines a second position stop member.

7. The transseptal puncture system of claim 6 wherein a distance of travel of the deployment member between the first and second position stop members defines the predetermined distance of the distal end of the needle member from the stowed position to the deployed position.

8. A transseptal puncture system for use in a heart having a septum, the transseptal puncture system comprising:

a needle member that includes a distal end and a proximal end, wherein the needle member defines a first lumen therethrough and defines a needle axis, wherein the needle member includes a cylindrical needle wall that includes inner and outer surfaces and a distal end, wherein the first lumen is defined by the inner surface of the needle wall, wherein the distal end of the needle wall includes an inner edge surface, an outer edge surface and a circular shaped transverse leading edge surface, wherein the inner edge surface is non-parallel with the outer edge surface, wherein the inner edge surface is curved and extends between the circular shaped transverse leading edge surface and the inner surface, wherein the outer edge surface is curved and extends between the circular shaped transverse leading edge surface and the outer surface, wherein a leading edge plane is defined by the circular shaped transverse leading edge surface, and wherein the leading edge plane extends perpendicular to the needle axis, and wherein the transverse leading edge surface has a transverse dimension that is equal to or less than half a thickness of the needle wall, a dilator that includes a distal end and a proximal end, wherein the dilator defines a second lumen therethrough, wherein the needle member is movable within the second lumen, and wherein the distal end of the needle member is configured to puncture the septum, a sheath that includes a distal end and a proximal end, wherein the sheath defines a third lumen therethrough, wherein the dilator is movable within the third lumen, a needle control device that is configured to move the needle member a predetermined distance from a stowed position to a deployed position, wherein the needle control device includes a deployment member that is movable between a first position and a second position, wherein movement of the deployment member from the first position to the second position moves the distal end of the needle member from the stowed position to the deployed position, wherein the deployment member is movable within a slot that includes a first position stop member and a second position stop member, wherein a distance of travel of the deployment member between the first and second position stop members defines the predetermined distance of the distal end of the needle member from the stowed position to the deployed position, and a guidewire that includes a distal end and a proximal end and is movable within the first lumen.

* * * * *